US006352856B1

(12) United States Patent
Falkner et al.

(10) Patent No.: US 6,352,856 B1
(45) Date of Patent: Mar. 5, 2002

(54) CHIMERIC POXVIRUS COMPRISING SEQUENCES OF A RETROVIRAL VECTOR COMPONENT (75) Inventors: Falko-Guenter Falkner, Orth/Donau; Georg Holzer; Friedrich Dorner, both of Vienna, all of (AT)

(73) Assignee: Baxter Vaccine AG, Vienna (AT)

( * ) Notice: Subject to any disclaimer, the term of this patent is extended or adjusted under 35 U.S.C. 154(b) by 0 days.

(21) Appl. No.: 09/228,625

(22) Filed: Jan. 12, 1999

(30) Foreign Application Priority Data

Jan. 16, 1998 (AT) .............................................. A 56/98

(51) Int. Cl.$^7$ ............................................... C12N 15/00
(52) U.S. Cl. ..................... 435/320.1; 435/455; 435/456
(58) Field of Search ........................... 435/235.1, 320.1, 435/440, 455, 456; 514/44, 93.1, 93.2

(56) References Cited

U.S. PATENT DOCUMENTS 5,494,807 A * 2/1996 Paoletti et al. ............. 435/69.3

FOREIGN PATENT DOCUMENTS

| | | |
|---|---|---|
| EP | 0711835 A1 | 5/1996 |
| WO | WO95/30018 | 11/1995 |
| WO | WO97/359996 | 10/1997 |

OTHER PUBLICATIONS

Chuah et al. Human Gene Therapy 6: 1363–1377 (1995).
Holzer et al. Virology 253: 107–114 (1999).
Wahlfors et al. Human Gene Therapy 8: 2031–2041 (1997).
M. Feng et al., "Stable in vivo gene transduction via a novel adenoviral/retroviral chimeric vector," Sep. 1997, Nature Biotechnology, vol. 15, pp.866–870.*
Vile, "A marriage of viral vectors," Sep. 1997, Nature Biotechnology, vol. 15, pp. 840–841.*
Verma et al. Gene Therapy–Promises, Problems, and Prospects. Nature, vol. 389, pp. 239–242, Sep. 18, 1997.*
Eck et al. Gene–Based Therapy. Goodman & Gilman's The Pharmacological Basis of Therapeutics, 9th Edition. Chapter 5, 1996.*
Hertig et al. Field and Vaccine Strains of Fowlpox Virus Carry Integrated Sequences from the Avian Retrovirus, Reticuloendotheliosis Virus. Virology, vol. 235, pp. 367–376, 1997.*
Bilbao et al. Faseb Journal, 11: 624–634 (1997).
Boshart et al. Cell 41: 521–530 (1985).
Caruso et al. Proc. Natl. Acad. Sci. USA 90: 7024–7028 (1993).
Coffin Virology, vol. 11, Chapter 58: 1767–1847 (1996).
Culver et al. Science 256: 1550–1552 (1992).
Davison et al. J. Mol. Biol. 210: 749–769 (1989).
Falkner et al. Journal Of Virology 62(6): 1849–1854 (1988).
Feng et al. Nature Biotechnology 15: 866–870 (1997).
Haffar et al. Journal Of Virology 64(6): 2653–2659 (1990).
Hirsch et al. Journal Of Virology 70(6): 3741–3752 (1996).
Holzer et al. Journal Of Virology 71(7): 4997–5002 (1997).
Ilan et al. Proc. Natl. Acad. Sci. USA 94: 2587–2592 (1997).
Isfort et al. Proc. Natl. Acad. Sci. USA 89: 991–995 (1992).
Karacostas et al. Proc. Natl. Acad. Sci. USA 86: 8964–8967 (1989).
Kurachi et al. Proc. Natl. Acad. Sci. USA 79: 6461–6464 (1982).
Li et al. Human Gene therapy 4: 403–409 (1993).
Miller et al. Journal Of Virology 70(8): 5564–5571 (1996).
Miller et al. Biotechniques 7(9): 980–990 (1989).
Moss Proc. Natl. Acad. Sci. USA 93: 11341–11348 (1996).
Noguiez–Hellin et al. Proc. Natl. Acad. Sci. USA 93: 4175–4180 (1996).
Paoletti Proc. Natl. Acad. Sci. USA 93: 11349–11353 (1996).
Pfleiderer et al. Protein Expression And Purification 6: 559–569 (1995).
Reiser et al. Proc. Natl. Acad. Sci. USA 93: 15266–15271 (1996).
Savard et al. Journal Of Virology 71(5): 4111–4117 (1997).
Vile Nature Biotechnology 15: 840–841 (1997).

* cited by examiner

*Primary Examiner*—Deborah Crouch
(74) *Attorney, Agent, or Firm*—Heller Ehrman White & McAuliffe

(57) ABSTRACT

A chimeric poxvirus is disclosed, which comprises the sequences of the vector component of a retroviral vector particle and optionally the packaging component of a defective retroviral particle. The chimeric poxvirus according to the invention particularly can be used for applications in gene therapy or tumor therapy.

15 Claims, 8 Drawing Sheets

| Adeno / Retrovirus- and Herpes / Retrovirus-System | Vaccinia System |

A  Introns

B  internal Polyadenylating sites

C  Ψ-Deletion by Splicing

Z, cell (cytosol); ZK, nucleus; FG, foreign gene; Ψ, packaging signal; i, intron; pA, polyadenylating signal

CHIMERIC POXVIRUS COMPRISING SEQUENCES OF A RETROVIRAL VECTOR COMPONENT

The invention relates to a chimeric poxvirus comprising the vector components of a retroviral (defective) genome. Furthermore, the invention relates to a chimeric poxvirus comprising the vector components and packaging components for producing retroviral defective viruses, as well as the use of the chimeric poxvirus according to the invention for gene or tumor therapy.

A central object of gene therapy is the stable genetic modification of target cells, and hitherto primarily viral vectors based on replication-deficient adenoviruses and retroviruses have been constructed for application in gene therapy.

The in vivo gene transfer with adenoviral vectors is very efficient, since particularly with adenoviral vectors, a large number of different cells can be transduced. However, in adenovirus infections, the DNA is not integrated into the host genome, but is present in episomal form. Moreover, a cellular immune reaction can be triggered which restricts the foreign gene expression (Li et al., 1993, Hum. Gene Ther. 4: 403–409). An attenuation of this reaction is possible by means of vectors in which the adenovirus E3 region has not been deleted (Ilan et al., 1997. Proc. Natl. Acad. Sci. USA 94: 2587 . 2592). These modifications allow for a transient expression of the therapeutic gene lasting for months. A permanent action, however, cannot be obtained with adenovirus vectors, since, as stated above, these vectors are not integrated into the genome of the host cell in a stable manner.

In contrast thereto, retroviral vectors are capable of integrating foreign genes into the genome of the host cell in a stable manner. Retroviruses belong to the few presently known viruses which have mechanisms for integrating foreign DNA into the genome of the host cell and thus are capable of permanently transforming the latter. On account of this property, they are frequently used in gene therapy approaches. For this purpose, in techniques used so far, foreign genes have been cloned into the proviral DNA of retroviruses, wherein, however, replication-deficient retroviruses have been used, in which at least one of the retroviral genes encoding for the packaging function (gag-pol or env) has been inactivated or deleted. These constructs contain the packaging signal psi and the flanking Long Terminal Repeat (LTR) sequences of the provirus. These transcription units are introduced into the cells with the plasmid vectors by conventional transfection techniques and commonly transcribed in RNA in the nucleus under the control of the LTR promoter. On account of the packaging signal psi, such an RNA is accepted as genomic viral RNA and packaged in retroviral particles.

To form infectious retroviral particles, in the simplest case, the gene products gag-pol and env must be present. These genes can be inserted into the cells also without the packaging signal via plasmid transfection, or they may be provided via a helper virus. For preparing retroviral particles, also cell lines in which the viral genes for the packaging components gag, pol and/or env are integrated in a stable manner and which express the same, can be transduced. Such cell lines are termed "packaging" lines and are described e.g. in WO 97/35996.

Plasmid constructs have been described, so-called "plasmoviruses", which encode all the necessary components for the formation of non-replicating retroviral particles (Noguiez-Hellin et al. 1996, Proc. Natl. Acad. Sci. USA 93: 4175–4180).

The use of replication-deficient retroviruses does, however, not completely prevent the risk that the retroviral DNA recombines with the helper genes, whereby it may come to the production of replication-competent viruses which possibly may have a tumorigenic potential.

Although the transformation of cells with retroviral vectors is highly efficient in vitro, difficulties are encountered at present in gene-therapeutical applications. Thus, transfection techniques as are required in the production of retroviral vectors via plasmid constructs, can only be carried out in vitro. The direct administration of the plasmid constructs for production of the defective retroviral particles in the body is extremely inefficient. Likewise, retroviral particles in vitro can be produced only up to comparatively low titers. On account of their instability, concentration of the particles is possible also to a limited extent only. The low titers and the instability of retroviral particles thus frequently prevent the efficient transformation in vivo. Methods, such as the direct injection of the particles into the target organ, or after tissue removal, ex vivo-transformation and implantation of transformed cells are being attempted at present. Also, the targeted transduction of certain target organs, the so-called "targeting", is very difficult in case of retroviral vectors. It has been attempted to change the tropism of the particles by heterologous enveloping proteins (pseudotyping).

The wide-spread retroviral vectors based on simple retroviruses, such as, e.g., Moloney Murine Leukemia Virus (MLV), are able to transduce only cells in the division phase. Cell growth in many fully grown organs is, however, very low. In tests for hepatic gene therapy, it has thus been attempted i.a. to obtain growing and thus transformable tissue by a partial removal of the liver. Likewise, retroviral vectors based on complex retroviral viruses, such as, e.g., HIV (lentiviral vectors) have been constructed, since the latter can also transform non-dividing cells (Reiser et al., 1996. Proc. Natl. Acad. Sci. USA 93: 15266–15271).

To correct the defective genes in case of gene therapy, an efficient insertion of the corresponding genes as well as long-term expression of the genes are particularly important. New approaches for preparing vectors for the stable in vivo-transduction thus take advantage of the principle of using viruses as the carriers for retroviral defective particles. In doing so, particularly the large insertion potential with DNA viruses, such as herpes virus and adenovirus, are utilized. The furthest-developed approach of chimeric virus systems is the preparation of defective retroviral particles by co-infection of two recombinant adenoviruses which encode the retroviral vector and the packaging function, respectively, the retroviral vector and the packaging proteins being introduced via the adenovector system, whereby these cells become transient retroviral production cells, and the retroviral vector particles formed therewith can infect the neighbouring cells (Feng et al., 1997. Nat. Biotechn. 15:866–870, Bilbao et al., 1997. FASEB J. 11:624–634).

This system has, however, several decisive disadvantages: The accepting capacity of foreign genes of adenovirus vectors is restricted to a few kilobases so that it is difficult to unite all the functions for producing a defective retrovirus (packaging components and retroviral vector components) in one adenovirus. Such a construct is, however, the prerequisite for an efficient in vivo gene therapy. Moreover, both adenovirus and retroviral genes and genomes are transcribed in the nucleus of the host cell and replicated, respectively. This topographic vicinity makes recombination to wild type retroviruses probable. In principle, this system also does not allow for a deletion of important retroviral transcription control regions, since the latter are necessary for the transcription in the nucleus. Thus, the adenovirus/ retrovirus system cannot be attenuated to the desired degree, in terms of safety technique. The same holds for the herpes simplex amplicon system; so far, the latter has only been described for the expression of retroviral structural proteins, wherein cells containing a lacZ provirus have been infected with an HSV amplicon vector containing the packaging components, and thus retroviral lacZ particles have been obtained (Savard et al., 1997. J. Virol. 71:4111–4117).

A disadvantage both with adenoviral and with retroviral vectors is in particular that introns for improving the foreign gene expression or for stabilising vector RNAs in the transduced cell cannot be applied since these introns have already been removed during the vector production by nucleus-specific splice mechanisms.

For a viral virus vector as a chimeric retrovirus carrier, also splicing and polyadenylating signals must be located at the correct site in the retroviral defective virus genome so as not to lead to a defective splicing or to a premature chain termination, respectively, during the transcription of the retroviral genomes to be transduced. If, for instance, the nuclear polyadenylating signal is put in front of the second, downstream retroviral LTR promoter, this will lead to a chain termination of the transcripts in the nucleus and to a retroviral defective genome no longer capable of transduction. In case of the atopic presence of these signals, the adeno- or herpes viruses replicating in the nucleus would not form a transducing defective retrovirus and cannot be made safer in this manner. The insertion of retroviral LTRs in herpes virus may, moreover, produce oncogenic subspecies from non-oncogenic herpes viruses (Isfort et al., 1992, Proc. Natl. Acad. Sci., USA 89;991–995). This is particularly possible because the life cycles of the herpes viruses are performed in the nucleus.

Also alpha viruses have been used as vectors for producing retroviruses. Coinfects of several Semliki Forest vectors obtained via RNAs synthesized in vitro resulted in infectious retroviral vector particles (Li et al., 1993. Hum. Gene Ther. 4:403–409). The natural tropism of carrier viruses could be used for the gene transfer into the respective preferred cell types and tissues.

It has been the object of the present invention to provide a vector system which does not have the above-mentioned disadvantages and allows for an efficient formation of retroviral particles.

According to the invention, this object has been achived by providing a chimeric poxvirus which comprises the sequences of the vector component of a retroviral particle.

By "vector component", in the present context a defective retroviral vector genome is understood which contains all the sequences necessary for the expression of the retroviral genome, including the packaging signal psi, as well as the sequences encoding a foreign protein. In the chimeric poxvirus of the invention, the sequence for the vector component in particular comprises a modified retroviral genome in which a foreign gene, in particular one (or several) sequence(s) encoding a foreign protein, antisense DNA, one (or several) ribozyme(s), are under the transcriptional control of a nucleus-active promoter, in particular a β-actin, CMV or SV40 early promoter.

The foreign protein may be any desired protein, a protein for substitution therapy or tumor therapy being, however, particularly preferred. Proteins suitable for substitution therapy may be plasma proteins, such as, e.g., factor II, factor V, factor VII, factor VIII, factor IX, factor X, factor XI, factor XIII, protein C, protein S, von Willebrand factor or erythropoetin. Proteins suitable for tumor therapy are tumor suppressor proteins, such as p53 or p73, or "suicidal genes", such as HSV TK, immunostimulators, such as B7.

The poxvirus-, in particular the vaccinia virus transcription apparatus recognizes neither the LTR promoter of the retroviral provirus DNA as promoter, nor does it recognize the proviral RNA processing signals. Thus, according to a special aspect of the present invention, the sequences of the vector component are put under the transcriptional control of a poxvirus-specific promoter.

There, particularly preferred promoters are poxvirus promoters which control the expression of the early genes. With the chimeric vaccinia virus of the invention (Retrovac vector), these are particularly the early promoters which comprise both natural and synthetic promoters, as described, e.g., by Davison et al. (1989, J. Mol. Bio. 210:749–769) and Pfleiderer et al. (1995, Protein Expr. Purif. 6:559–569).

To prepare such constructs, e.g., the U3-region from the 5' end of the proviral DNA can be deleted and replaced by a poxvirus-specific promoter. Likewise, the U5-region from the 3' end of the proviral DNA can be deleted and a TTTTTNT signal can be added at the end of the "R" region. The repeated regions "R" at the ends of the transcripts are essential to the reverse transcription and thus to the functionality of the vector particles. Initiation upstream of the normal transcription start leads to the synthesis of a transcript having a non-repeated 5' end, and thus, as expected, to reduced vector titers. With a view to a correct 5' end of the RNA, the initiation site of the poxvirus promotor each inserted in the prototype construct should thus be optimized in each case. Optimisation of such constructs is within the general knowledge of the skilled artisan and can be carried out without great expenditures.

With the chimeric poxvirus according to the invention, defective retroviral particles can be prepared in a simple manner by infection of suitable packaging cell lines, such as, e.g., described in WO 97/35996, which express the packaging components.

According to a special embodiment of the present invention, the chimeric poxvirus contains the sequences which encode the vector components and the packaging components.

The chimeric poxvirus according to the invention, comprising both the vector component and the packaging component, is capable of liberating recombinant defective retroviruses in situ, since it expresses in the target cell both the genes for the packaging components and also a transcription unit which encodes a retroviral defective genome. Besides retroviral replication signals and packaging signals, the retroviral defective genome preferably also comprises the foreign gene to be transduced and expressed, which is controlled either by the promoter of the retroviral long terminal repeat (LTR) itself, or by a second promoter.

Within the present invention, by "packaging component" any genes necessary for forming a retroviral vector, such as gag-pol and env, of a retrovirus are understood. For the construction of the chimeric poxviruses of the invention (so-called RetroVac vectors), simple retroviruses, such as MLV, just as well as complex retroviruses, e.g. human immunodeficiency virus (HIV) can be used. Likewise, for changing the host spectrum, heterologous enveloping proteins (VSV-G, e.g.) can be expressed for the transforming retroviral particles, as has already previously been described for retroviral vectors. Generally, most of the further developments on retroviral vectors can also be applied to Retro-Vac vectors. This also includes the expression of foreign genes under the control of tissue-specific promoters and vectors for the site-specific integration of foreign DNA.

According to the invention, the gag, pol and env genes preferably are under the control of a poxvirus promoter. Preferred are promoters having a large early portion, in agreement with the expression characteristic of the poxvirus. The sequences gag/pol and env encoding the packaging components can be expressed in one transcription unit or on separate transcription units under the control of a poxvirus/vaccinia virus-specific promoter, wherein the transcription unit may be integrated in an essential or non-essential region of the poxvirus genome.

With poxvirus transcripts, splicing does not take place. Retroviral genes whose expression encompasses splicing, thus, according to a further aspect of the present invention, are cloned as intron-free reading frames into the chimeric poxvirus of the invention. Depending on the retroviral system selected, this aplies to the genes env, tat, ref or other ones.

With the chimeric virus according to the invention, defective retroviral particles can be produced in a simple manner both in vitro and in vivo. So far, no system has been described in which all the components for a defective retroviral particle have been encoded and combined on one single carrier virus. This is an essential pre-requisite for the efficient application of such vectors in vivo.

The development of packaging vectors and delivery/amplification systems of transducing defective retroviruses on the basis of chimeric poxviruses so far has not been described. What has been described, however, is the use of poxvirus vectors for the expression of retroviral components, in particular of gag-pol and env of HIV in poxvirus vectors (Moss, 1996, Proc. Natl. Acad. Sci., USA 93: 11341–11348, Paoletti, 1996, Proc. Natl. Acad. Sci., USA 93: 11349–11353). The purpose of these studies was, however, fundamental virological research and vaccine development. Thus, e.g., it is known that the expression of the HIV-1 gag-pol reading frame in VV (vaccinia virus) leads to the formation of pseudoparticles (Karacostas et al., 1989, Proc. Natl. Acad. Sci., USA 86:8964–8967). Likewise, the co-expression of gag and env leads to the formation of HIV-like particles which are particularly suitable for vaccine development (Haffar et al., 1990, J. Virol. 64: 2653–2659). Also the double-expression of gag-pol and env in poxvirus vectors as SIV candidate vaccine has been described (Hirsch et al., 1996, J. Virol. 70:3741–3752).

As the vectors for the chimeric poxviruses according to the invention, in particular chordopox viruses are used, which also include viruses from the group of the orthopox viruses and of the avipox viruses (Moss, 1996, Poxviridae: the viruses and their replication. In: Fields et al. (ed.) Fields Virology. Third Edition ($3^{rd}$. Ed.) Vol. 2. Lippincott-Raven, Philadelphia, 2637–2671). Preferably, however, such poxviruses are used which infect mammalian cells, yet do not propagate therein (non-replicating vectors). As the vectors, thus preferably vaccinia viruses are used, in particular attenuated vaccinia viruses (Paoletti, 1996, Proc. Natl. Acad. Sci., USA 93: 11349–11353), Modified Vaccinia Ankara (MVA), or defective vaccinia viruses, such as described in WO 95/30018 and in Holzer et al. (1997, J. Virol, 71:4997–5002). The last-mentioned defective virus vector can easily be propagated to titers of $10^8$ plaque forming units (PFU)/ml and concentrated to titers of $10^{11}$ PFU/ml. Moreover, e.g., D4-deleted defective viruses remain in the early phase of replication, which leads to a lasting synthesis of early RNAs. Only early vaccinia virus (VV)-RNAs have defined 5' and 3' ends, which is a basic pre-requisite for the synthesis of functional retroviral genoms. A vaccinia virus defective particle which expresses the entire genetic information for a retroviral vector causes the formation of non-replicating retroviral particles in the infected cell, which particles in turn have a transforming potential. Since, as stated above, particularly vaccinia viruses can be concentrated to titers of $10^{11}$ PFU/ml, the titer, based on the transformation (expressed in CFU/ml) is thus higher than conventional retrovirus titers ($>10^6$–$10^7$). By the expression of retroviral particles in situ, furthermore all the transforming particles released over time are relevant for the transduction and not, as in with the in vitro production of retroviruses, the transducing particles per volume of cell culture supernatant.

According to a special embodiment of the present invention, a non-replicating vaccinia virus, such as described in WO 95/30018, serves as the carrier of the genetic information for non-replicating defective retroviruses. Both the modified retroviral genome which contains the foreign gene and the packaging signal psi, and the retroviral genes gag-pol and env are encoded on the genome of a defective vaccinia virus. The sequences gag/pol and env encoding the packaging component can be expressed in one transcription unit or in several transcription units under the control of a poxvirus/vaccinia virus-specific promoter and can be integrated in an essential or non-essential region of the poxvirus genome. The sequences of the vector component can be inserted as an autonomous transcription unit, also under the control of a poxvirus, preferably an early poxvirus promoter, in an essential or non-essential region of the recombinant virus, insertion in an essential region being preferred.

The DNA sequence TTTTTNT leads to a termination of the early poxvirus/vaccinia transcription. To efficiently express the retroviral sequences, thus TTTTTNT signals possibly present in the retroviral sequences or in the foreign gene, respectively, should be modified by point mutation without changing the amino acid context of the retroviral proteins or destroying the controlling signals on the RNA genome of the defective retroviruses, such as e.g. psi, and the integration region "att".

According to a special embodiment of the present invention, thus the sequences encoding the packaging components and the vector components, respectively, do not comprise any poxvirus/vaccinia virus-specific stop signals.

Just as for the expression of the vector component sequence, in the chimeric poxvirus-RetroVac system of the invention it is preferred to put the vector component sequence under the transcriptional control of a poxvirus-specific promoter.

In the preferred chimeric defective vaccinia virus constructs described in the present invention, downstream of the 3' region a signal was inserted for the termination of early vaccinia virus transcripts, and thus the 3' end of the mRNAs forming differ from that of previously described retroviral vector genomes. Only with the so-called early vaccinia mRNAs, most of them have a defined 3' end. Late vaccinia mRNAs which constitute the major portion of the viral transcripts do not terminate at concrete signals, have heterogenous lengths and thus are not suitable as retroviral vector genomes. D4-defective VV do not enter the late phase of replication. This could be demonstrated by $^{35}$S labelling experiments of proteins and in Northern Blot experiments by an unexpectedly long lasting early expression (Holzer et al., 1997, J. Virol. 71:4997–5002). Thus they proved to be a tool unique among poxviruses, for the synthesis of defined retroviral genomes.

One advantage of the chimeric poxviruses according to the invention is that they can be propagated and concentrated to very high virus titers. Moreover, the vectors derived from poxvirus, in particular vaccinia virus, are extremely stable, efficiently infect organs, such as liver or spleen, and produce transforming, yet not replicating, retroviral particles directly in the target organ (in vivo amplification of the retroviral particles).

Since poxviruses are tissue-specific (primary affine organs), a transformation is effected by the chimeric poxvirus of the invention, in particular the chimeric vaccinia virus, in a tissue-specific manner. For instance, the infection with the chimeric vaccinia virus (RetroVac hybrid vectors) preferably takes place in those tissues which correspond to the tropism of vaccinia virus, and which also express the receptors for the retroviral enveloping proteins used. Via suitable combinations of the vaccinia virus strain used and pseudotyping, a more stringent targeting of both the therapeutic gene and of the retroviral vectors can be achieved.

The chimeric poxvirus vectors, in particular the RetroVac vectors based on defective vaccinia virus, combine the ability of retroviruses to integrate foreign DNA in target cells in a stable manner with the technical advantages of poxvirus/vaccinia vectors. A main characteristic of the system is that when a host cell is infected by the chimeric poxvirus, in particular a RetroVac vector based on a vaccinia virus vector, the proteins necessary for the formation of functional retroviral particles are expressed and the mRNAs containing the foreign genes are transcribed and packaged as genomic RNA in retroviral particles. These particles are not capable of propagating (replication-deficient), yet they do have a transforming potential. While the cells primarily infected with the chimeric poxvirus, in particular with the chimeric vaccinia virus, will die, secondary retroviral infection of further cells by the retroviral particles formed will lead to a permanent integration of the retroviral sequences, and thus of the sequences encoding the foreign gene, into the cell genome.

The liberation of defective retroviral particles by the chimeric poxviruses of the invention has been surprising insofar as normally the transcription of retroviruses as well as the capping of the genomic RNAs occur in the nucleus (Coffin, 1996, Retroviridae: the viruses and their replication. In: Fields et al. (ed.) Fields Virology. Third Edition ($3^{rd}$ Ed.) Vol. 2, Lippincott-Raven, Philadelphia, 1767–1847). In the chimeric poxvirus system shown, transcription and capping occur in the cytoplasm. The vaccinia virus-specific cap structures thus are no obstacle for a retroviral packaging. Surprisingly it has been found that transcripts generated by the cytoplasmatic poxvirus/vaccinia transcription system are compatible with the retroviral transcription and replication system. This was unexpected insofar as the polyadenylating signals which are recognized in the nucleus are located within the U3 and R regions of the provirus.

As a rule, poxviruses are lytic viruses, whereby cells which have been infected by a chimeric poxvirus will die in most instances. On account of the lesions thus caused in the tissue, division of neighbouring cells can because which thus become even more susceptible to retroviral transformation by the retroviral particles formed. In case of ectodermal cells, this proliferation effect is increased by growth factors of the poxvirus itself.

In a special embodiment, thus the chimeric poxvirus according to the invention comprises sequences encoding a growth factor or a mitogen. By this, the proliferation effect of the neighbouring cells of the poxvirus-infected cells can be increased by the expression of chimeric poxvirus.

In a further special embodiment, it is possible to construct RetroVac vectors on the basis of lentiviruses, in which, however, accessory lentivirus genes must be expressed in the VV carrier, which give the system the properties desired.

In contrast to plasmid transfection, chimeric adenovirus/retrovirus vectors or chimeric herpes virus/retrovirus vectors, expression by vaccinia virus occurs in the cytoplasm of the host cell. While after a plasmid transfection or in case of an adenovirus/retrovirus infection the transcription of the foreign genes occurs in the nucleus by aid of the cellulary transcription apparatus, the gene expression of vaccinia virus exclusively occurs in the cytosol, by means of a viral transcription apparatus different from the cellular one. This constitutes a decisive safety advantage of the poxvirus vector of the invention insofar as by this the generation of replicating retroviruses becomes very unlikely. This approach for the first time allows for the arrangement of nuclear transcription signals on the retroviral genome exclusively according to the point of view of optimal foreign gene expression and of the safety in the transduced target cell, since the transcription of genomic retroviral RNA by vaccinia virus occurs independently of the nucleus of the target cell. Likewise, introns can be used to enhance the expression of a therapeutic gene, since the former do not influence vector RNA expression in the vaccinia virus system.

A further particular advantage of the virus vector system of the invention based on a DNA virus replicating in the cytoplasm is that, contrary to viruses propagating in the nucleus, retroviral transcription units may contain transcription signals which normally are not allowed or not possible in connection with the nucleus, since splicing does not occur in the life cycle of a cytoplasmatically transcribing virus vector. Thus, in the RetroVac system, e.g., the retroviral packaging signal psi can be flanked by splicing signals, which, after transduction of the retroviral defective genomes and transcription of the same in the host will lead to RNAs which have no packaging signals and thus have lost an essential feature of retroviral genomes (cf. FIG. 2C). This possibility substantially increases the safety of the system of the retroviral defective genomes produced in the poxvirus system. The functionality of the packaging signal outside of the wild type context has already been shown.

Figure 1:
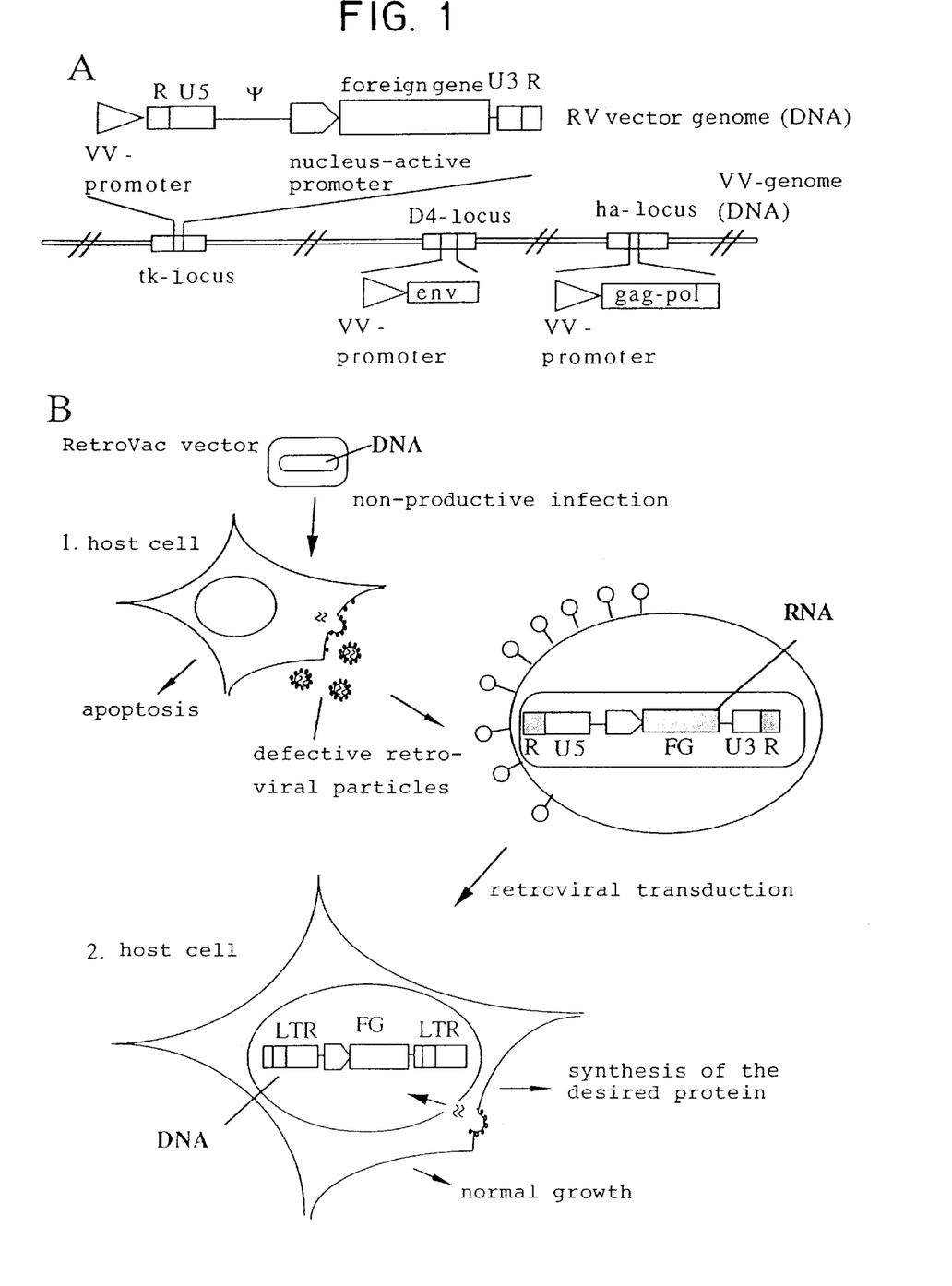
Figure 2:
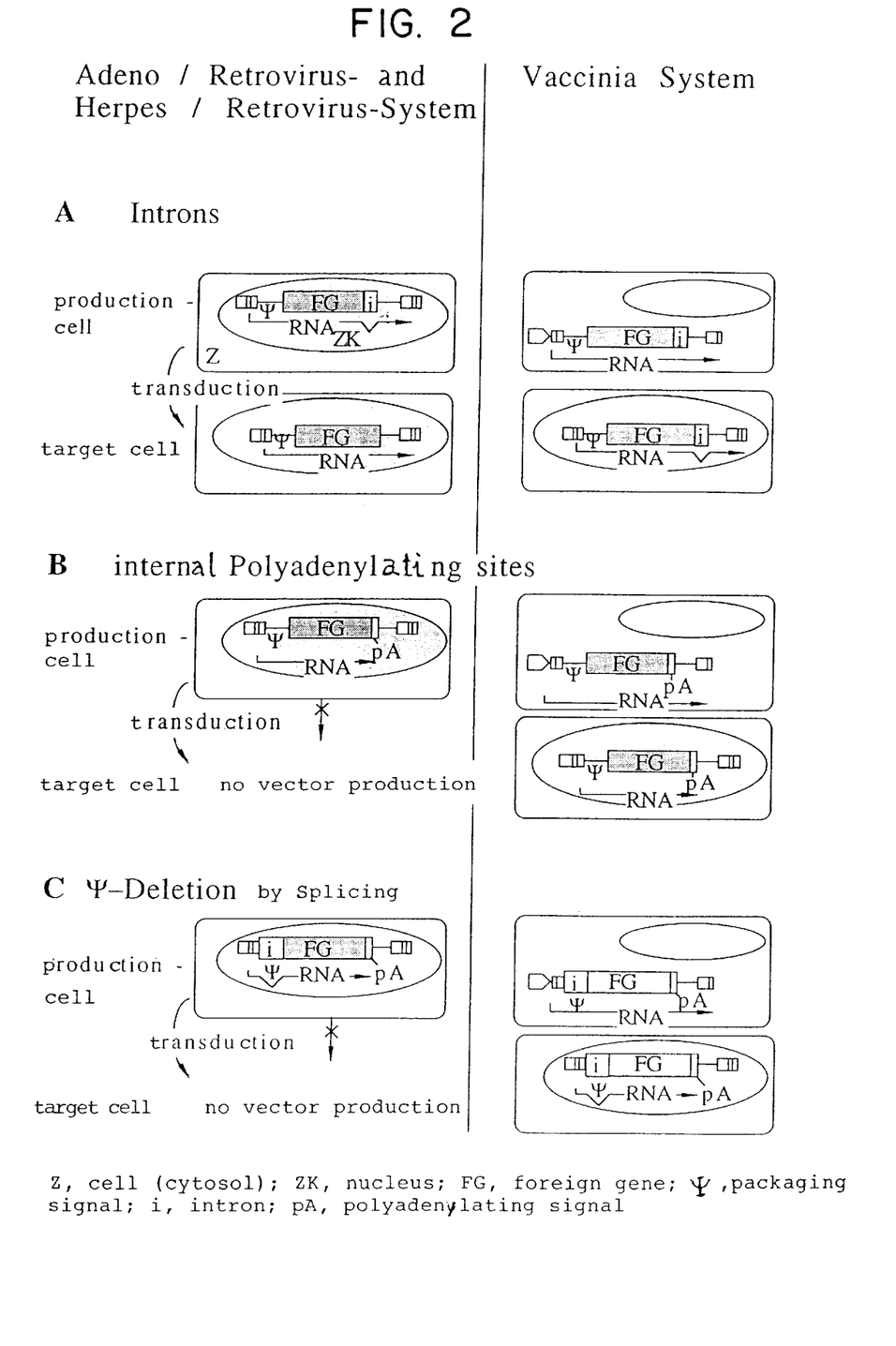

A further aspect of the present invention is that in case of a cytoplasmatic transcription of the retroviral defective RNAs, established transcription units having intron-exon structure can be integrated undamaged (without splicing) into the genome of the host via retroviral transduction (cf. FIG. 2A). When establishing permanently expressing cell lines, as a rule gene cassettes are transferred, consisting of promoter, open reading frame (ORF) of the foreign gene, intron and polyadenylating signal, cloned into a bacterial plasmid. For an optimal mRNA production, introns are required in transcription units, in particular this has also been observed in transgenic animals. Most of the commercially available expression vectors for higher cells contain empirically determined promoter-intron combinations within their expression cassettes; e.g., the CMV promoter/enhancer SV40 intron combination in vector pCMVβ (Clontech Laboratories, Palo Alto) has proved successful. Such optimized units having intron-exon structure cannot be transduced via the hitherto known retroviral or chimeric, respectively, gene transfer vectors.

The RetroVac system according to the invention solves this problem, since on account of the missing splicing apparatus, no introns are removed in the vaccinia virus during the transcription. After transduction of the retroviral defective genome produced in the RetroVac system, the complete transcription unit thus can be integrated in the target cell (cf. FIG. 2A). This is particularly important at the transfer of cDNAs difficult to be expressed for the purpose of gene therapy, such as those of the coagulation factor VIII, and allows for the transfer of optimized promoter/intron combinations.

According to a special aspect of the invention, thus by the system according to the invention defective retroviral particles comprising an intron-containing genome are provided.

An RNA processing signal which may be transferred into the target cell at a defined site merely by cytosolic transcription systems is an internal polyadenylating signal which causes a defined termination of the transcript in the nucleus (FIG. 2B). Termination of the transcript before completion of a complete retroviral defective genome in the nucleus, such as by transduction of retroviral defective genomes produced in the RetroVac system, allows for a particularly safe gene therapy, since the foreign gene once integrated cannot be transduced further, because its transcript terminates prematurely. Likewise, the localisation of the packaging signal between splice signals (FIG. 2C) is possible only in the RetroVac system, which, in the target cell, leads to the transcription of retroviral defective genomes which lack the packaging signal. Thus, in combination with internal polyadenylating signals, particularly safe gene cassettes can be transferred.

A further aspect of the present invention relates to a composition comprising a chimeric poxvirus of the above-defined type and a pharmaceutical carrier.

The RetroVac system according to the invention can be utilized in all applications for which a gene therapy with retroviruses is meaningful. It is suitable for the in vivo gene therapy for the treatment of plasma protein defects, in particular hemophilias (factor IX and factor VIII deficiencies) and erythropoetin deficiency. Administration may be intravenously or intramuscularly.

With an appropriate formulation, the stability of the chimeric poxviruses according to the invention also allows for an oral administration of the vectors as sprays, which enables inhalation treatment of cystic fibrosis.

A further application of the RetroVac vectors is tumor therapy. It has been shown, for instance, that the transfer of so-called suicide genes into tumors or their metastases has proven to be promising in animal experimental models (Caruso et al., 1993, Proc. Natl. Acad. Sci., USA 90: 7024–7028, Culver et al., 1992, Science 256:1550–1552). In such experiments, the HSV-TK gene which converts nontoxic nucleoside analogs (such as Ganciclovir) into toxic ones, was transduced by intratumoral injection of packaging cell lines which in situ liberate defective retroviral particles, and subsequently a chemotherapy was carried out with Ganciclovir. With the RetroVac vector of the invention, thus suicide genes can safely and more efficiently be administered.

Likewise, apoptosis-induced tumor-suppressor genes, such as, e.g., the p53 gene which is altered in more than 50% of the tumors, can be inserted as foreign gene in the RetroVac vector of the invention. At the gene-therapeutical transfer of these tumor suppressor genes, the tumor cells would stop their growth on account of the endogenous control.

An ex vivo cell transduction for tumor therapy (e.g. leukemia) likewise is possible; furthermore, the direct intratumoral injection for cancer therapy.

To increase the safety of the system, vectors can be used which carry the so-called suicide genes, such as, e.g., the herpes simplex virus (HSV) with an inserted thymidine-kinase gene, which would allow for a chemotherapy, if there were an activation of oncogens in vivo due to the transduction procedure.

The system can also be used for producing permanent cell lines, since retroviral particles allow for a particularly efficient transduction and since on account of the transfer of RNA processing signals (introns, polyadenylating sites) optimal gene cassettes can be transferred. In this manner, the highly efficient transfer of gene cassettes has been possible for the first time, which in connection with screening techniques allows for the rapid identification of highly expressing cell clones.

A special aspect of the present invention thus relates to the use of the chimeric poxvirus according to the invention for producing a medicament, which in particular can be used for gene therapy and tumor therapy.

Within the scope of the present invention, defective retroviral particles were obtained via the above-mentioned chimeric poxviruses, which are particularly characterized in that they still comprise an intron-containing genome.

The invention will now be explained in more detail by way of the following Examples and the drawing figures, to which, however, it is not restricted.

FIGS. 1(A–B) shows the schematic representation of the construction of chimeric vaccinia virus. FIG. 1A shows the possible insertion position of the packaging and vector components, which optionally may be integrated in different regions of the poxvirus genome and which are under the transcriptional control of a poxvirus promoter. FIG. 1B shows the infection diagram of a cell with the poxvirus of the invention, and the production of defective retroviral particles which in turn infect cells and integrate into the host genome in a stable manner.

FIGS. 2(A–C) shows a comparison of a chimeric poxvirus replicating in cytoplasm with the system of adeno or herpes viruses, respectively, which replicate in the nucleus, in particular with a view to the splicing mechanism.

FIGS. 3(A–B) shows the construction diagram of plasmid pTKgpt-LSXN.

FIGS. 5(A–B) shows the construction diagram of plasmid pTK-MLVg.

EXAMPLE 1

Construction of the vaccinia virus (VV)-defective virus vd-LXSN.

In the retroviral defective virus genome of the proviral vector plasmid pLXSN (Miller et al., 1989, Biotechniques. 7:980–990) the early vaccinia virus (VV) transcription stop signals were removed, and the thus deleted genome was cloned behind a strong VV early promotor and then inserted into the thymidine-kinase (tk) locus of the VV defective virus strain vD4-vA (Holzer et al., 1997, J. Virol. 71:4997–5002). In doing so, retroviral defective genomes were transcribed in the early VV infection cycle in the resultant VV defective virus vd-LXSN.

Construction of the plasmid pTKgpt-LXSN

The retroviral defective genome in plasmid pLXSN (Clontech Laboratories, Inc., Palo Alto, Calf.) has the following order of genetic elements: LTR-psi-MCS/SV40-neo-gene-cassette-LTR (LTR, long terminal repeat; psi, packaging signal for retroviral RNA; MCS, multiple cloning site; SV40-neo, SV40 promoter neomycin resistence gene cassette). Into the MCS of this construct, suitable foreign genes can be inserted; the SV40-neo gene cassette serves as the selection marker by aid of which the retroviral transduced cells can be selected.

The proviral retroviral DNA in pLXSN has three TTTTTNT signals which lead to a partial termination of the early transcription. Individual fragments were cloned by PCR and modified by mutagenesis (FIG. 3). For this, the following 3 PCR fragments were amplified by means of different oligonucleotides, with the plasmid pLXSN as template, and in doing so, point mutations were introduced which modify the TTTTTNT signals present. The preparation of the fragments LX1, LX2 and LX3 was effected as described in the following:

LX1: A 1.6 kb fragment was generated with the oligonucleotide primers oRV-5 (5'-TACGTACGGC GCGCCAGTCT TCCGATAG-3') and oRV-6 (5'-GAACCGGTCG CCCCTGCGCT GAC-3'), wherein an SnaBI cleavage side was introduced by oRV-5 and an AgeI cleavage site was introduced by oRV-6.

LX2: A 1 kb fragment was generated with the oligonucleotide primers oRV-7 (5'-AGACGTCCCA GGGACTTTGG GGGCCGTATT TGTGGC-3') and oRV-8 (5'-AGGCCGAGGC GGCCTCGGCC TCTGCATAAA TAAATAAAAT TAG-3') and the TTTTTNT motive was modified by the two primers by means of point mutations; oRV-7 binds in the region of an AatII cleavage site, oRV-8 in the region of an SfiI cleavage site.

LX3: The 3' end of the planned vector construct was generated as the 1.2 kb PCR fragment with the oligonucleotide primers oRV-9 (5'-CGACCGGTTC TATTTGTCAA GACCGACCT-3') and oRV-10 (5'-GCGGCCGCAA CTGCAAGAGG GTTTATTGGA-3'). oRV-10 binds at the 3' end of the "R" sequence and introduces a NotI cleavage site.

To modify a TTTTTNT signal in the neo reading frame, a mutagenesis was carried out in plasmid PLXSN. The mutagenesis was made by means of the QuickChange™ mutagenesis kit of Stratagene and the primers oRV-35 (5'-AAATAGAACC GGTCGCCCCT GCGCTGAC-3') and oRV-9. The resultant plasmid was named pLXSNmut (FIG. 3b) and comprises a PinAI cleavage site at the mutagenised site.

The LX1 PCR product was cloned into the vector pCRII (Invitrogen), the plasmid which contained the PCR product in the desired orientation was selected and termed pCR-LX1(b). The LX2 PCR product was cleaved with the enzymes AatII and SfiI and inserted into AatII and SfiI cleaved pCR-LX1(b). The resultant plasmid was identical to pCR-LX1(b) except for the modified TTTTTNT signals and was termed pCR-LX4. The ligation of a 1.4 kb SfiI/SacI fragment from the plasmid pLXSNmut in SfiI/SacI cleaved pCR-LX4 yielded pCR-LX4+. This plasmid contains the entire transcribed region of the vector, except for the outermost 3' end.

Figure 3A:
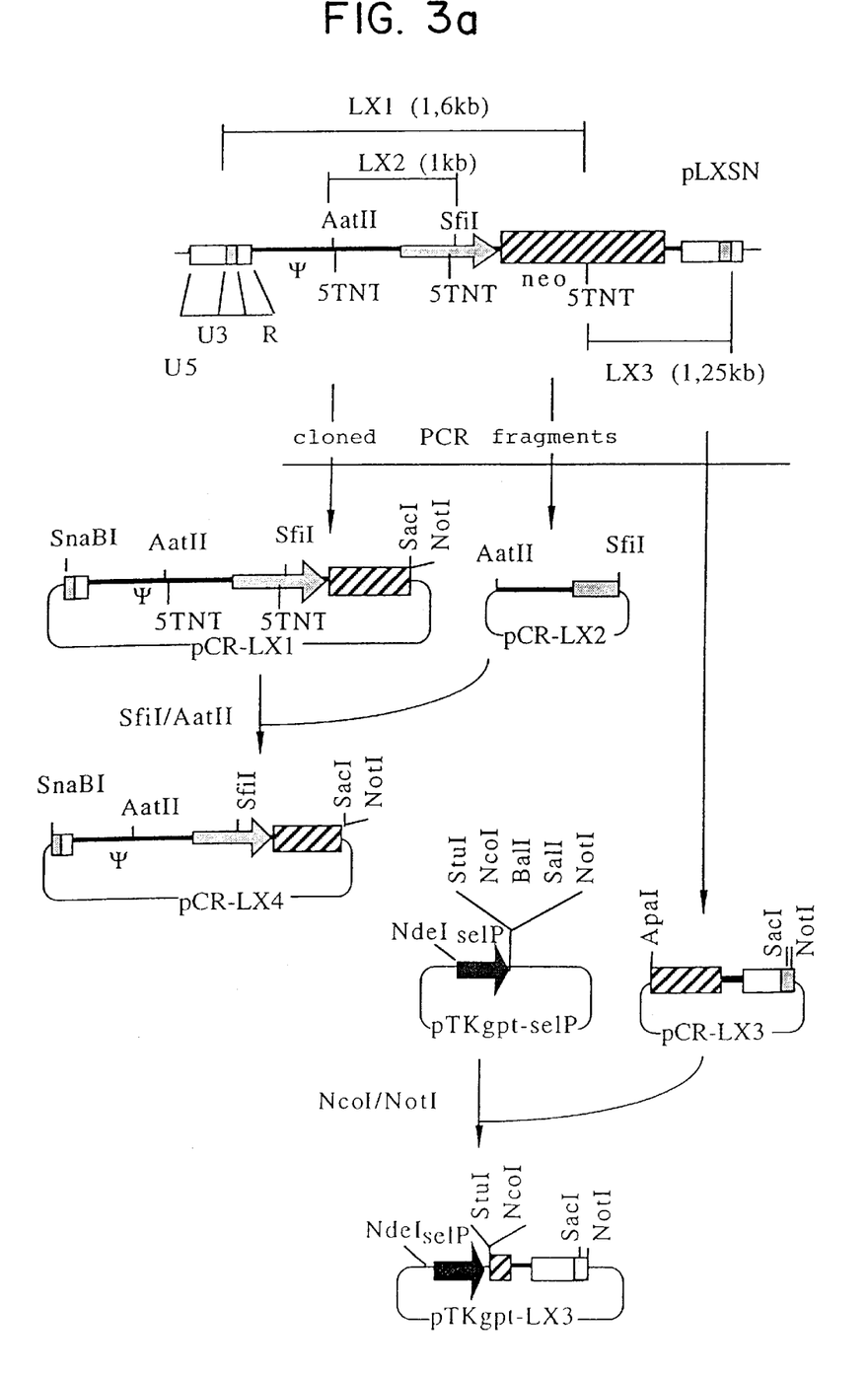
Figure 3B:
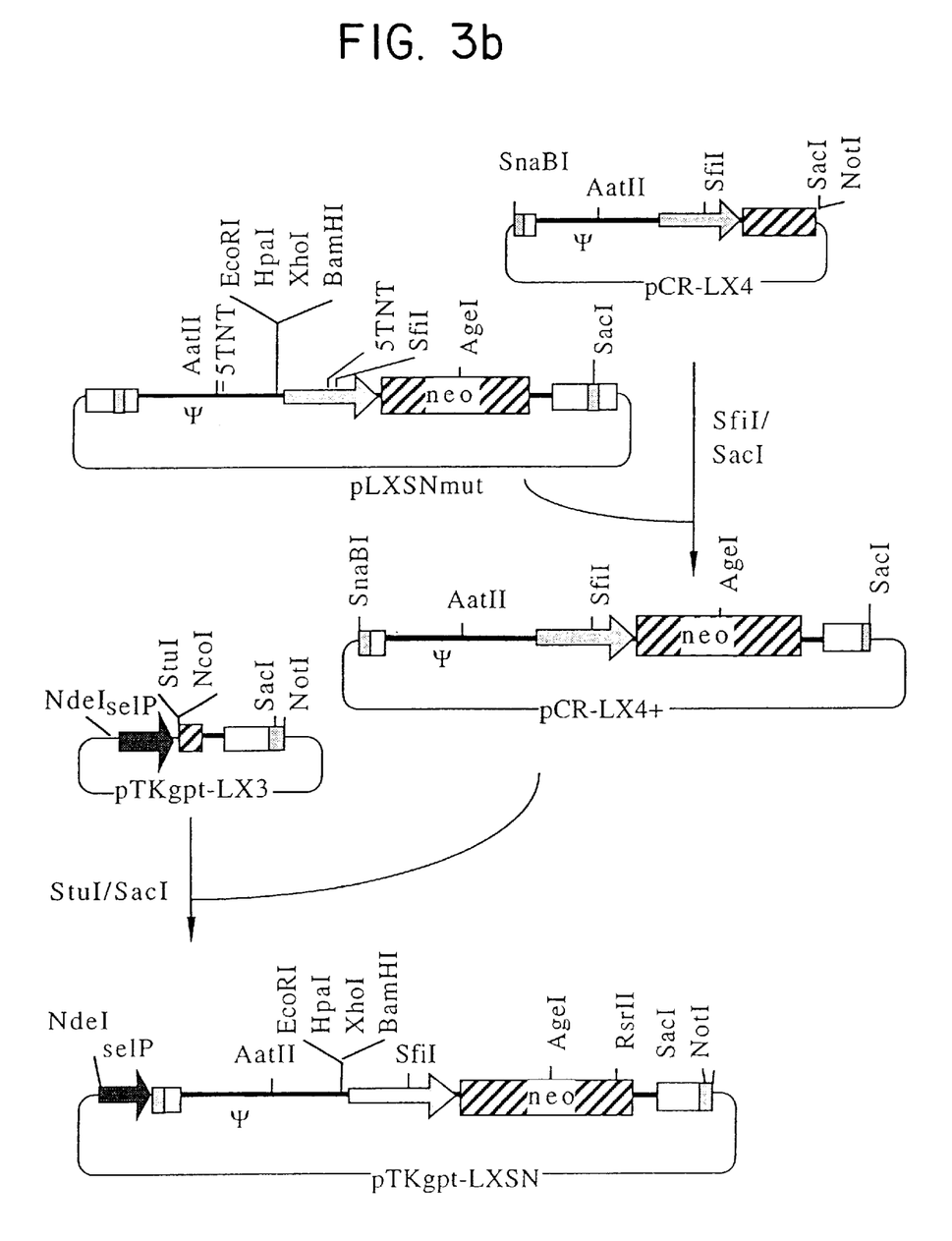

The correct 3' end was inserted as 0.8 kb fragment from pCR-LX3 into the VV recombination vector pTKgpt-selP (Pfleiderer et al., 1995, Protein Expr. Purif. 6:559–69). The plasmid obtained was termed pTKgpt-LX3 (FIG. 3a). The plasmid vector pTKgpt-LXSN was obtained by cleaving a 2.7 kg SacI/SnabI fragment out of pCR-LX4 and cloning into pTKgpt-LX3 cleaved with SacI and StuI, and, under the control of a strong VV promoter, it contained the entire transcribed region of the vector pLXSN from the beginning of the "R" sequence (Coffin, J. M., 1996, Retroviridae: The viruses and their replication, p. 1767–1847. In: Fields et al. (ed.) Fields, Virology, 3$^{rd}$ ed. Vol. 2, Lippincott-Raven, Philadelphia) in the 5' LTR up to the end of the "R" sequence in the 3' LTR, wherein the three originally present TTTTTNT motives are modified (FIG. 3b).

Construction of the VV defective virus vd-LXSN

To construct the VV defective virus vd-LXSN, RK-D4R-44.20 cells were infected according to the standard protocol with the defective-VV vD4-vA (Holzer et al., 1997, J. Virol. 71:4997–5002) and transfected with the plasmid pTKgpt-LXSN. Virus isolates were plaque-purified in RK-D4R-44.20 cells under gpt selection (Falkner et al., 1988, J. Virol. 62:1849–1854). The thus obtained VV defective virus vd-LXSN expresses the entire defective retroviral RNA genome of pLXSN. The correct genomic structure of vd-LXSN was proven in Southern blot and by PCR.

EXAMPLE 2

Production of defective retrovirus particles by means of the VV defective virus vd-LXSN in the packaging cell line PT67.

The defective virus vd-LXSN contains and transcribes a retrovirus defective genome (cf. Example 1). The cell line PT67 (obtained from Clontech Laboratories, Inc., Palo Alto, Calf.) expresses the gag-pol and env genes of murine leukemia virus (MLV) which are needed for packaging retroviral defective genomes (Miller et al., 1996, J. Virol. 70:5564–71). To check the hypothesis that defective VV in the presence of gag-pol- and env-proteins can form defective retrovirus particles, PT67 cells were infected with vd-LXSN. Cultivation of the PT67 cells was effected according to standard conditions, as described in RetroXpress System User Manual. Clontech Laboratories, Inc., Palo Alto, Calif., 1997. The infection with vd-LXSN was effected at 0.05 or 0.5 PFU (plaqueforming units) per cell. At various points of time (3 h to 72 h post infection), the retroviral vector particles were titrated in the supernatants of NIH-3T3 cells (ATCC CRL-1658) in the presence of 500 µg/ml G418 (Miller et al., 1996, J. Virol. 70:5564–71). The retroviral titers reached a maximum 6 h post VV infection and in this range were each independent of the vd LXSN infection dose. In a typical experiment, with a primary infection of 0.5 PFU vd-LXSN per cell, after 3 h $10^2$ CFU (colony forming units), and after 6 h $2 \times 10^2$ CFU were counted per ml of culture supernatant. Control experiments with the plasmid pLXSN resulted in $10^2$ CFU-$10^3$ CFU per ml, 48 h post transfection. The retrovirus titers which were induced by vdLXSN infection, dropped to 20 CFU/ml at 12 h post infection, to rise again to a maximum of $2 \times 10^2$ CFU/ml at 48 h to 72 h pi. This second rise was not dependent on the initial infection dose and is attributed to a retrovirus-mediated transformation of VV uninfected PT67. No retroviral particles were obtained after transfection of the plasmid pTKgpt-LXSN in PT67, which proves that the expression of this construct, other than, e.g., with adenovirus carriers, is possible only in the viral context. This example shows that defective VV are suitable as carriers of transducing retroviral defective genomes. The result is surprising insofar as normally the transcription of retroviruses as well as the capping of the genomic RNAs occurs in the nucleus (Coffin et al., supra) . In the RetroVac system shown, transcription and capping occur by means of vaccinia-encoded enzymes in the cytoplasma. The VV speficic cap structures apparently are no obstacle to a retroviral packaging.

EXAMPLE 3

Construction of the VV defective virus vd-e10A1

Figure 4:
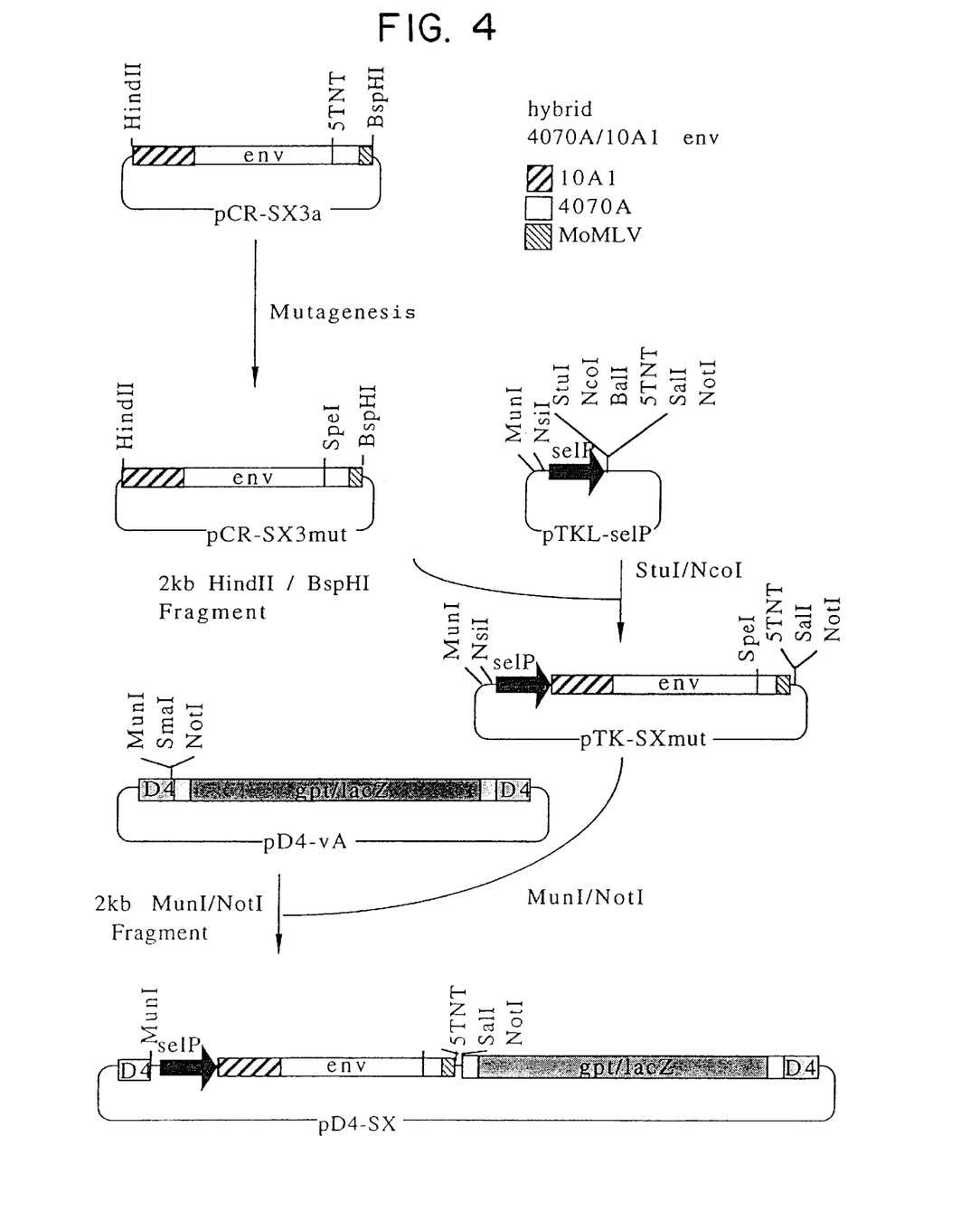
FIG. 4 shows the construction diagram of plasmid pD4-SX.

In Examples 1 and 2 it has been shown that defective VV which transcribe retroviral genomes, form functional defective retroviruses in packaging cell lines. In the following, the 10A1 env gene was expressed in the D4 locus of VV, a further step for combining all the components for the formation of defective RV particles on one defective VV. Cloning was effected in intermediate steps, since one TTTTTNT motive of the env region had to be deleted (FIG. 4).

Construction of the plasmid pD4-SX

Plasmid pCR-SX3mut: the MLV env gene (env SX: hybrid from the strains 4070A and 10A1) was amplified as the 2 kb PCR product with the primers oRV-37 (5'-TCAGGGTCGAC ATGGAAGGTC CAGCGTTCTC-3') and oRV-38 (5'-GACTTTCATG ACTATGGCTC GTACTC-TATA GGCTTC-3') from the cell line PT67 (Miller et al. 1996, J. Virol. 70:5564–5571) and cloned into the plasmid vector pCRII. A TTTTTNT signal in the env reading frame was modified by mutagenesis on this plasmid. Mutagenesis was effected by means of the QuickChange™ mutagenesis kit of Stratagene, and the primers oRV-41 (5'-GAATGTTGTT TCTATGCAGA CCACACGGGA CTAGTGAGAG-3') and oRV-42 (5'CTCTCACTAG TCCCGTGTGG TCTGCATAGA AACAACATTC-3'). The resultant plasmid was termed pCR-SX3mut. Plasmid pTK-SXmut: From plasmid pCR-SX3mut, the env reading frame was cleaved out as 2 kb fragment with the enzymes BspHI and HindII and ligated into the NcoI- and StuI-cleaved plasmid pTKL-selP, whereby plasmid pTKSX-mut was obtained.

Plasmid pTKL-selP: In plasmid pTKgpt-selP (Example 1), an 0.3 kb fragment was replaced via the cleavage sites HindIII and NdeI by a synthetic linker with the oligonucleotides oRV-22 (5'-AGCTCGCAAT TGATGCATCA CA-3') and oRV-23 (5'-TATGTGATGC ATCAATTGCG-3') and the additional cleavage sites NsiI and MunI were inserted.

Plasmid pD4-SX: An expression cassette comprised of the strong VV promoter selP and the env reading frame was cleaved out of plasmid pTK-SXmut with the enzymes MunI and NotI, and ligated into MunI/NotI-cleaved pD4-vA (21). The resultant vector pD4-SX (FIG. 4) thus comprises the described expression cassette between flanking sequences of the VV-D4 locus. Integration of this DNA in VV thus yields defective, non-replicating recombinants which express the env gene.

Construction of the VV defective virus vd-e10A1

The homologous recombination of pD4-SX with the VV wild type Western Reserve (WR) strain was effected according to standard techniques in RK-D4R-44.20 cells. Plaque purification was effected in RK-D4R-44.20 cells twice with gpt selection and screening for lacZ-positive plaques and twice without selection and screening for lacZ negative plaques (Holzer et al., 1997, J. Virol. 71:4997–5002). The resulting isolates were termed vd-e10A1. A control of the env expression was effected in the Western blot. An MoMLV-specific antiserum was obtained from Quality Biotech/Camden, N.J. (SerumID: 81S000044 "disrupted virus").

EXAMPLE 4

Construction of the VV defective virus vd-eg

The MLV gag-pol reading frame was inserted into the hemagglutinin gene locus of the VV vector vd-e10A1 (Example 3). Thus, a defective VV forms which expresses both gag-pol$^{MLV}$ and env$^{10-A1}$ and is capable of forming pseudoparticles. This MLV packaging vector still comprises a free thymidine-kinase gene locus into which retroviral defective genomes comprising foreign genes suitable for gene therapy can be inserted (as described in Examples 5 and 6).

Figure 5A:
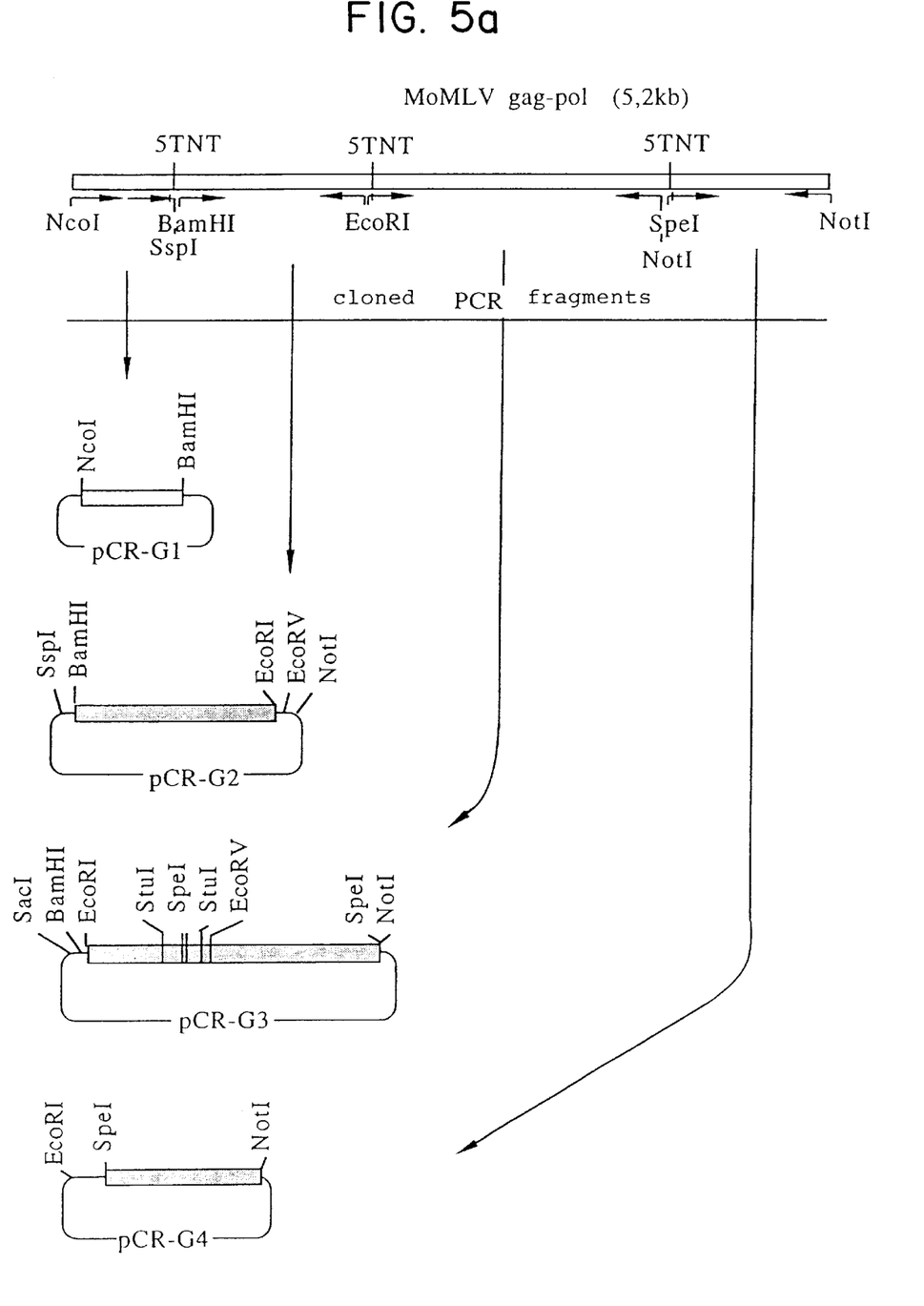
Figure 5B:
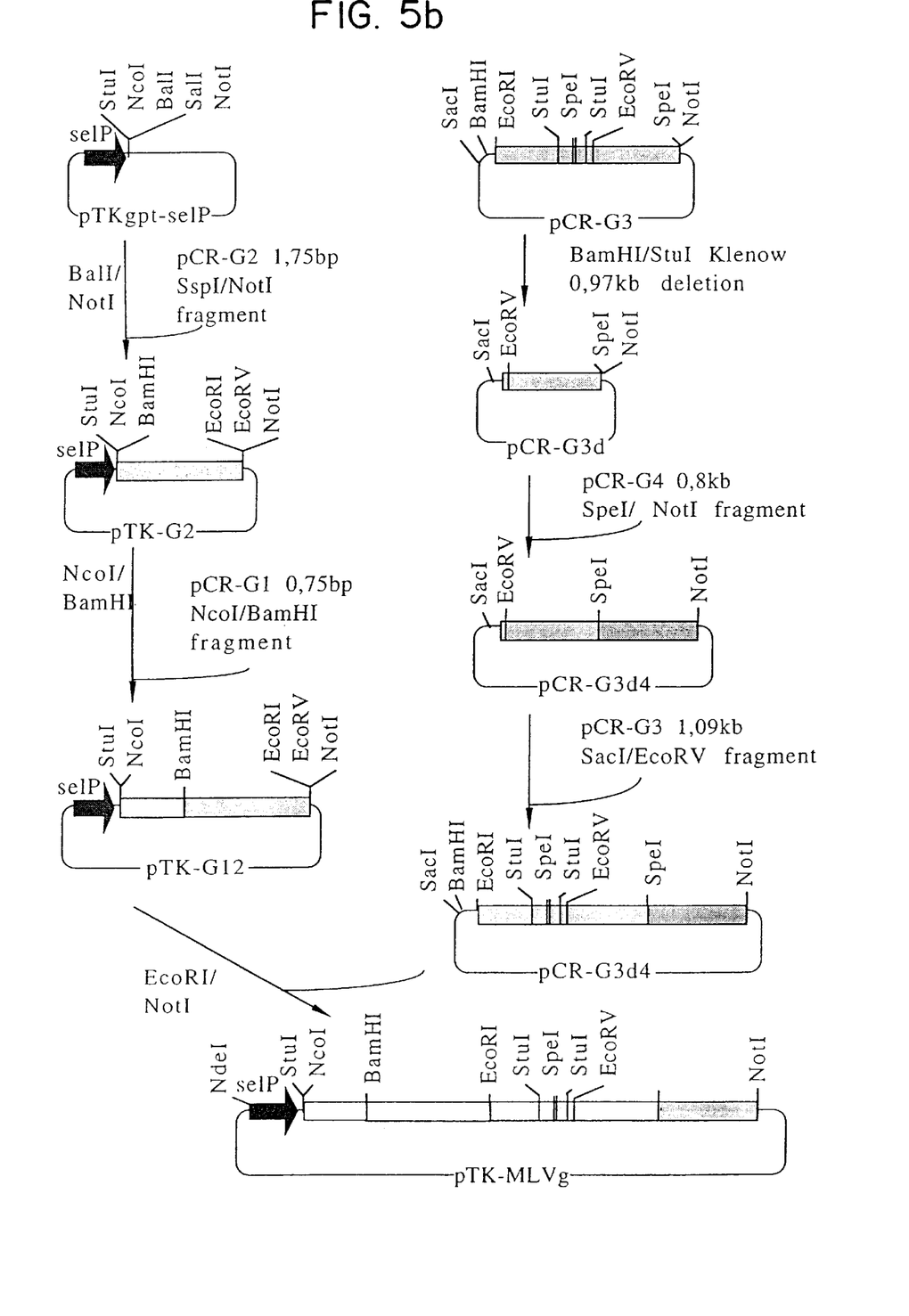

Cloning is effected in intermediate steps, since three TTTTTNT motives of the gag-pol region had to be deleted (FIGS. 5a and 5b).

The MLV gag-pol reading frame (5.2 kb) was amplified via PCR from the packaging cell line PT67 (Clontech Laboratories, Inc., Palo Alto, Calif.). For this, four PCR fragments (G1–G4) were amplified which overlap at their ends. By the primers, the three TTTTTNT motives present were modified, and compatible cleavage sites were generated without influencing the amino acid sequence.

Amplification of the fragment G1: With the oligonucleotide primers oRV-11 (5'-CCATGGGCCA GACTGTTACC ACT-3') and oRV-12 (5'-CTGGATCCTC AGAGAAAGAA GGGTT-3'), an 0.8 kb fragment was generated from MLV gag-pol, wherein by means of oRV-11 an NcoI cleavage site and by means of oRV-12 a TTTTTNT signal was mutated and a BamHI cleavage site was introduced.

Amplification of the fragment G2: With the oligonucleotides oRV-13 (5'-ATTAACCCTT CTTTTTCTGA GGATCCAGGT-3') and oRV-14 (5'-CATCCTTGAA TTCAAGCACA GTGTACCACT G-3', a 1.7 kb fragment was generated from MLV-gag-pol, wherein a BamHI cleavage site was introduced by the oligonucleotide oRV-13, as well as an additional SspI cleavage site which it has at its 3' end; by oRV-14, an EcoRI cleavage site is introduced.

Amplification of the fragment G3: With the oligonucleotide primers oRV-15 (5'-TGAATTCAAG GATGCCTTCT TCTGCCTGA-3') and oRV-16 (5'-AACTAGTAGA TATT-TATAGC CATAC-3') a 2 kb fragment was generated from MLV-gag-pol, wherein oRV-15 mutates a TTTTTNT signal and introduces an EcoRI cleavage site; by oRV-16, a SpeI cleavage site and an additional NotI cleavage site which it has at its 3' end, are introduced.

Amplification of the fragment G4: With the oligonucleotides oRV-17 (5'-ATATCTACTA GTTTTCATAG ATACCT-3') and oRV-18 (5'-GCGGCCGCTT AGGGGGC-CTC GCGGGTTA-3'), an 0.8 kb fragment was generated from MLV gag-pol, wherein a TTTTTNT motive was modified by oRV-17 and a SpeI cleavage site and by oRV-18 a NotI cleavage site were introduced.

Cloning of the plasmids pTK-MLVg and pHA-MLVg

The G2 PCR fragment was cloned into the vector PCRII (Invitrogen, Inc) (pCR-G2), and from this again isolated via the enzymes SspI and NotI (FIG. 5a). Ligation in the BalI- and NotI-cleaved vector pTKgpt-selP yielded the plasmid pTK-G2 (FIG. 5b). The G1 PCR product was cleaved out of pCR-G2 by means of the enzymes NcoI and BamHI, isolated, and ligated into the NcoI- and BamHI-linearized plasmid pTK-G2, whereby the plasmid pTK-G12 was obtained (FIG. 5b).

The G3 PCR product was ligated into the vector pCRII so as to obtain pCR-G3. By digestion with the enzymes BamHI and StuI, Klenow treatment and religation, a 1 kb sequence was deleted from pCR-G3, and into the thus-obtained plasmid pCR-G3d, the 0.8 kb-sized G4 PCR product was inserted via the cleavage sites SpeI and NotI. The resultant plasmid was termed pCR-G3d4. Insertion of a 1.1 kb fragment obtained by digestion of pCR-G3 with the enzymes SacI and EcoRV into the SacI-and EcoRV-cleaved plasmid pCR-G3d4 yielded the plasmid pCR-G34, which comprises the 3' half of the MLV gag-pol reading frame. A 3 kb fragment was digested via the EcoRI and NotI cleavage sites, and was recloned into the plasmid pTK-12 by religation of pCR-G34. In the resultant plasmid pTK-MLVg, the entire MLV gag-pol reading frame downstream of the strong early-late VV promoter selP is contained (FIG. 5b).

The plasmid pTK-MLVg was cleaved with NdeI (partially) and NotI, and the selP-gag-pol cassette was isolated as 5.3 kb fragment. The fragment was Klenow-treated and ligated into the SnaBI-linearized VV integration plasmid vector pHA-vA. The resultant plasmid was termed pHA-MLVg.

Construction and functionality test of the packaging vector vd-eg.

The homologous recombination of the plasmid-DNA pHA-MLVg and the starting virus vd-e10A1 (Example 3), as well as the plaque purification were effected according to the standard protocol in RK-D4R-44.20 cells (Holzer et al., 1997, J. Virol. 71:4997–5002.). The gag-pol expression was confirmed in the Western blot. The gag-pol- and env-expressing isolates were termed vd-eg.

Furthermore, the functionality of the expressed retroviral genes was tested on 3T3 cell clones which had been obtained by transformation with the retroviral vector pLXSN. For this, 3T3 cells were transformed with defective LXSN retrovirus, as described in RetroXpress System User Manual. Clontech Laboratories, Inc., Palo Alto, Calf. (1997). Five G418-resistant clones were isolated. The supernatants of these cultures were not infectious, and thus could not cause a transduction of native 3T3 cells. These lines were infected with recombinant viruses vd-eg (moi=1). After three days, the supernatants were harvested and used for the transformation of 3T3 cells. The transformation experiments were effected as described by Miller et al. (1996. J. Virol. 70: 5564–5571). The thus transformed 3T3 cells were G418-resistant, the supernatants of selected clones were not transforming. The transformation observed thus was not caused by a re-activation of retroviruses capable of propagation. This experiment proves that expression of the retroviral genes by the packaging vector vd-eg enables the packaging of transforming retroviral defective genomes.

EXAMPLE 5

Construction of the RetroVac vector vd-egLXSN

With vd-egLXSN as the starting vector, a VV vector was constructed which expresses all the components necessary for the formation of transducing defective retroviral particles. The preparation of vd-egLXSN was effected via homologous recombination with the plasmid-DNA pTKgpt-LXSN (Example 1) and the packaging virus vd-eg (Example 4) according to the standard protocol in RK-D4R-44.20 cells (cf. Example 1). Isolates were purified in several plaque purification rounds in RK-D4R-44.20 cells under gpt selection and termed vd-egLXSN. With sucrose gradient-purified virus stocks of vd-egLXSN, 3T3 and RK13 cells were infected (moi=1). After 6 h, the supernatants were harvested and tested for transformation of 3T3 cells analogous to Example 1. Depending on the cell line, the supernatants of $10^6$ cells contained between $10^2$ and $10^3$ CFU retroviral vector. This Example proves that the infection of wild type cells with the RetroVac vector vd-egLXSN suffices to express transforming retroviral vector particles.

Example 6

Construction of a RetroVac vector vd-egC9 which expresses dRV particles with factor IX cDNA insert.

In the following experiment, the human coagulation factor FIX is cloned into a RetroVac vector, and retroviral defective particles are produced which are suitable for the gene therapy of hemophilia B. For this purpose, a gene cassette comprised of the cytomegalovirus (CMV) promoter/enhancer (Boshart et al., 1985. Cell. 41:521–530) and the coagulation factor FIX-cDNA and genetic elements (the "FIX gene cassette", as described in EP 0 711 835), which allow for RNA processing, and inserted into the plasmid pTKgpt-VP. The resultant plasmid pTKgpt-VP-FIX is recombined in the tk locus of the packaging vector vd-eg, resulting in the RetroVac vector vd-egC9.

Construction of the plasmid pTKgpt-VP-FIX

Figure 6:
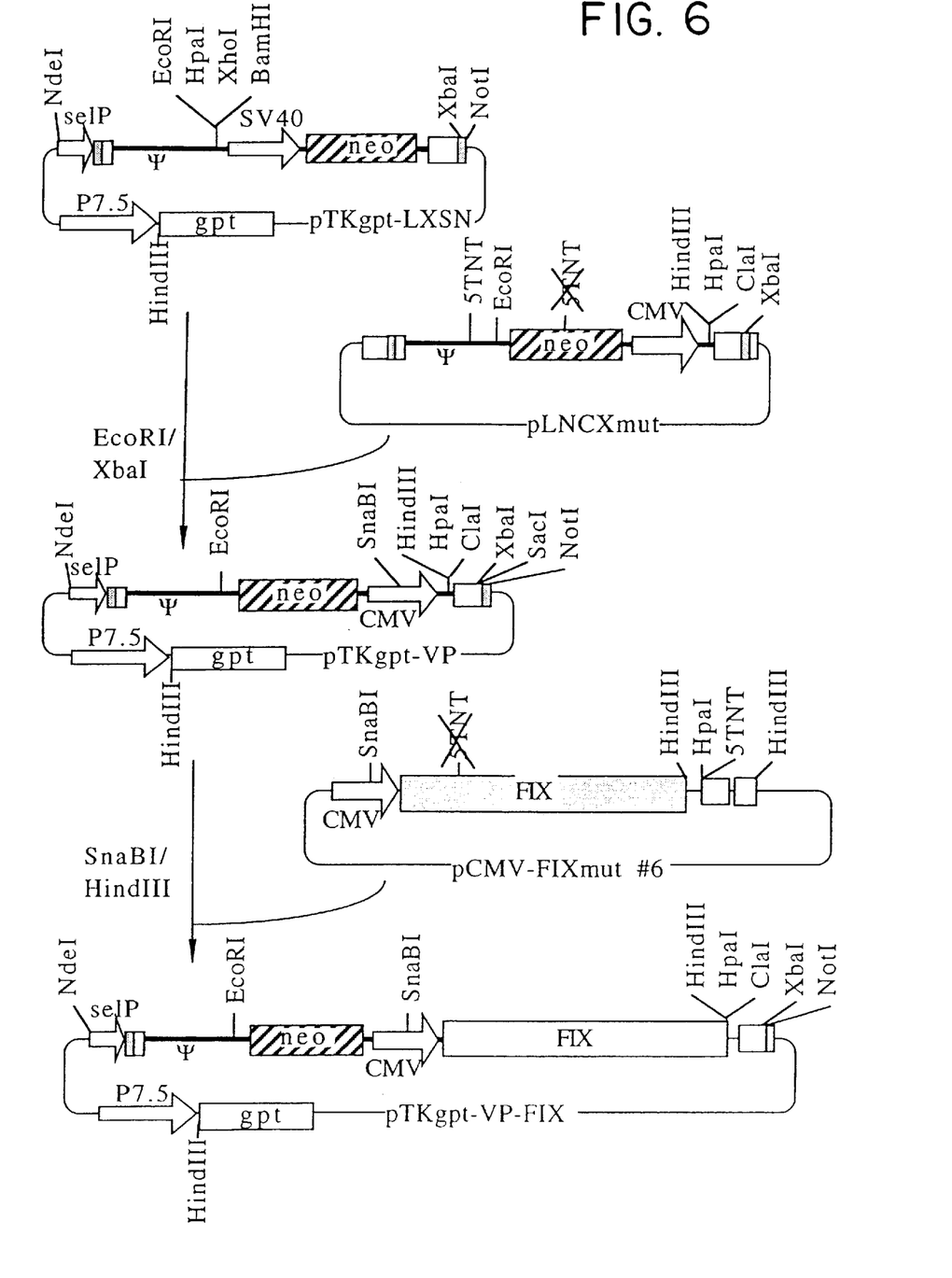
FIG. 6 shows the construction diagram of plasmid pTKgpt-VP-FIX.

The factor IX-cDNA (Kurachi et al., 1982, proc. Natl. Acad. Sci., USA, 79:6461–6464) comprises a TTTTTNT motive, which was modified via mutagenesis with the primers omut.FIX-1 and omut.FIX-2 (FIG. 6). The resultant plasmid was termed pCMV-FIXmut.

pTKgpt-VP. Analogous to pTKgpt-LXSN, a plasmid vector was constructed on the basis of PLNCX for VV expression. A TTTTTNT motive in the neomycin resistance gene of PLNCX was mutagenized for this purpose (primer oRV-35 and oRV-9). The right half of the retroviral vector sequence was transferred from this mutagenized plasmid pLNCXmut via the cleavage sites EcoRI and XbaI into the vector pTKgpt-LXSN. The resultant plasmid was termed pTKgpt-VP and comprises the elements VV-thymidine-kinase (tk) gene flank/VV promoter selP/ RV-'R'/RV-u5/psi/ Neo/CMV promoter/MCS/RV U3/RV-'R'/TTTTTNT/VV-tk flank.

For constructing plasmid pTKgpt-VP-FIX, a SnaBI/HindIII fragment which comprises a part of the CMV promoter and the entire FIX-cDNA was put from pCMV-FIXmut into SnaBI/HindIII (partial digestion)-cleaved pTKgpt-VP.

Construction and test of the RetroVac vector vd-egC9.

The plasmid pTKgpt-VP-FIX was recombined in the packaging vector vd-eg according to standard methods and plaque-purified (cf. Example 5). The resultant virus was termed vd-egC9. Sucrose gradient-purified stocks of vd-egC9 were prepared to infect 3T3 and RK13 cells (moi=1). After 3 days, the supernatants were harvested and tested for transformation of 3T3 cells analogous to Example 4. Depending on the line, the supernatants of $10^6$ cells contained between $10^2$ and $10^3$ CFU retroviral vector. Infection of half-confluent RK13 (ATCC CCL-37) or SK-HEP-1 (ATCC HTB-52) cells with the supernatants which contained retroviral FIX defective particles, expressed functional factor IX (measured as described in EP 0 711 385).

EXAMPLE 7

Infusion of the RetroVac vector vd-egC9 in rabbits, and detection of human factor IX in rabbit plasma.

In the following experiment it is shown in the animal test that the RetroVac vector vd-egC9 permits the expression of factor IX in vivo.

New Zealand white rabbits were administered $10^8$ and $10^9$ pfu vd-egC9 intravenously, and for a period of one month, blood was drawn every second day and human factor IX was quantitated in ELISA. Pre-infusion sera were taken to determine, whether or not the ELISA is specific for the human factor IX. Human factor IX could be found in rabbit plasma at concentrations sufficient for a hemophilia B therapy. The presence of anti-human plasma protein antibodies was determined after four weeks in Western blots. In a control experiment, (infection with the defective virus vD4-vA), no human factor IX could be detected).

What is claimed is:

1. A chimeric poxvirus comprising a poxvirus genome comprising stably inserted therein a replication defective retroviral proviral genome under transcriptional control of a promoter, wherein a foreign gene sequence under transcriptional control of a promoter is inserted into said retroviral genome.

2. The chimeric poxvirus as set forth in claim 1, further comprising a packaging component sequence.

3. A chimeric poxvirus as set forth in claim 1, wherein said poxvirus is a chordopox virus.

4. A chimeric poxvirus as set forth in claim 1, wherein said poxvirus is an orthopox virus.

5. A chimeric poxvirus as set forth in claim 4, wherein said orthopox virus is a vaccinia virus.

6. A chimeric poxvirus as set forth in claim 6, wherein said vaccinia virus is a defective vaccinia virus.

7. The chimeric poxvirus as set forth in claim 1, wherein said retroviral genome is under transcriptional control of a poxvirus promoter.

8. The chimeric poxvirus as set forth in claim 2, wherein said packaging component sequence is under transcriptional control of a poxvirus promoter.

9. The chimeric poxvirus as set forth in claim 7, wherein said poxvirus promoter is an early poxvirus promoter.

10. A chimeric poxvirus as set forth in claim 8, wherein said poxvirus promoter is an early poxvirus promoter.

11. The chimeric poxvirus as set forth in claim 1, wherein said retroviral genome sequence comprises introns.

12. The chimeric poxvirus as set forth in claim 1, wherein said retroviral genome sequence comprises an internal polyadenylation sequence.

13. A defective retroviral particle comprising an intron-containing genome.

14. A method for producing a defective retroviral particle comprising a foreign gene sequence, wherein the method comprises infecting a cell of a packaging cell line with a chimeric poxvirus comprising a poxvirus genome having stably inserted therein a replication defective retroviral genome under transcriptional control of a promoter, wherein a foreign gene sequence under transcriptional control of a promoter is inserted into said retroviral genome, and wherein the infected cell produces a defective retroviral particle.

15. A method for producing a defective retroviral particle comprising a foreign gene sequence, wherein the method comprises infecting a cell of a cell line with a chimeric poxvirus comprising a poxvirus genome having stably inserted therein a replication defective retroviral genome under transcriptional control of a promoter, wherein a foreign gene sequence under transcriptional control of a promoter is inserted into said retroviral genome and retroviral packaging components under transcriptional control of a promoter, and wherein the infected cell produces a defective retroviral particle.

* * * * *